United States Patent
Wenger

(10) Patent No.: US 10,470,913 B2
(45) Date of Patent: Nov. 12, 2019

(54) ANKLE BRACE FOR ANKLE-FOOT ORTHOTIC

(71) Applicant: Core Products International, Inc., Osceola, WI (US)

(72) Inventor: Jerry A. Wenger, Powell, WY (US)

(73) Assignee: Core Products International, Inc., Osceola, WI (US)

( * ) Notice: Subject to any disclaimer, the term of this patent is extended or adjusted under 35 U.S.C. 154(b) by 247 days.

(21) Appl. No.: 15/378,241

(22) Filed: Dec. 14, 2016

(65) Prior Publication Data

US 2017/0165096 A1   Jun. 15, 2017

Related U.S. Application Data

(60) Provisional application No. 62/266,887, filed on Dec. 14, 2015.

(51) Int. Cl.
*A61F 5/01* (2006.01)
*A43B 7/20* (2006.01)

(52) U.S. Cl.
CPC ............. *A61F 5/0113* (2013.01); *A43B 7/20* (2013.01)

(58) Field of Classification Search
CPC ..... A61F 5/0111; A61F 5/0113; A61F 5/0116; A61F 5/0109; A61F 5/0127; A61F 5/0585; A61F 5/0195; A43B 7/20
See application file for complete search history.

(56) References Cited

U.S. PATENT DOCUMENTS

| | | | |
|---|---|---|---|
| 1,282,066 | A | 10/1918 | Gerits |
| 1,894,183 | A | 1/1933 | Lindner |
| 2,584,010 | A | 1/1952 | Goffredo |

(Continued)

FOREIGN PATENT DOCUMENTS

| | | |
|---|---|---|
| EP | 1501456 | 2/2005 |
| EP | 1562526 | 8/2005 |

(Continued)

OTHER PUBLICATIONS

Application and File History for U.S. Appl. No. 14/754,830, filed Jun. 30, 2015, inventor Wenger.

(Continued)

*Primary Examiner* — Kari K Rodriquez
(74) *Attorney, Agent, or Firm* — Patterson Thuente Pedersen, P.A.

(57) ABSTRACT

A customizable ankle-foot orthotic. The orthotic including an ankle brace for installation around a wearer's ankle, the ankle brace including a first wing, a second wing, and a third wing anchored at a point between the first wing and the second wing, the second and third wings independently configurable to couple to a portion of the first wing to enable the wearer to customize the fit; a tension adjustment assembly including one or more strap loops; and an elastic strap operably linking the ankle brace to a wearer's shoe for applying an upward resistive force to the wearer's shoe to prevent inadvertent downward movement of a wearer's foot, the elastic strap threadable through the one or more strap loops such that the elastic strap wraps around the exterior face of the ankle brace and extends at a downward angle to engage the wearer's shoe.

19 Claims, 10 Drawing Sheets

(56) References Cited

U.S. PATENT DOCUMENTS

| | | | |
|---|---|---|---|
| 3,527,209 | A * | 9/1970 | Baker ................ A61F 5/0113 602/28 |
| 3,834,377 | A | 9/1974 | Lebold |
| 3,916,886 | A | 11/1975 | Rogers |
| 3,976,059 | A | 8/1976 | Lonardo |
| 4,554,912 | A | 11/1985 | Haberman |
| 4,817,589 | A | 4/1989 | Wertz |
| 5,020,523 | A | 6/1991 | Bodine |
| RE33,762 | E | 12/1991 | Lonardo |
| 5,219,324 | A | 6/1993 | Hall |
| 5,224,925 | A | 7/1993 | Yarn |
| 5,259,834 | A | 11/1993 | Wittmeyer |
| 5,269,748 | A | 12/1993 | Lonardo |
| 5,277,699 | A | 1/1994 | Williamson |
| 5,298,013 | A | 3/1994 | Lonardo |
| 5,306,230 | A | 4/1994 | Bodine |
| 5,370,604 | A | 12/1994 | Bernardoni |
| 5,425,701 | A * | 6/1995 | Oster ................ A61F 5/0111 128/882 |
| 5,430,960 | A | 7/1995 | Richardson |
| 5,449,339 | A | 9/1995 | Drennan |
| 5,603,692 | A | 2/1997 | Maxwell |
| 5,700,237 | A | 12/1997 | Hess |
| 5,704,140 | A * | 1/1998 | Fields ................ A43B 7/1495 36/132 |
| 5,817,041 | A | 10/1998 | Bader |
| 5,860,423 | A | 1/1999 | Thompson |
| 5,943,793 | A | 8/1999 | Clements |
| 6,102,881 | A | 8/2000 | Quackenbush et al. |
| 6,146,349 | A | 11/2000 | Rothschild et al. |
| 6,695,797 | B2 | 2/2004 | Trieloff |
| 6,926,687 | B2 | 8/2005 | Shields |
| 6,945,947 | B2 | 9/2005 | Ingimundarson et al. |
| D514,225 | S | 1/2006 | Sassi |
| 7,077,818 | B2 | 7/2006 | Ingimundarson et al. |
| 7,094,213 | B1 | 8/2006 | Cook |
| 7,458,950 | B1 | 12/2008 | Ivany |
| 7,666,158 | B2 | 2/2010 | Jacobsen et al. |
| 7,674,212 | B2 | 3/2010 | Kruijsen et al. |
| 7,722,556 | B2 | 5/2010 | Warner |
| 7,918,765 | B2 | 4/2011 | Kruijsen et al. |
| 8,114,042 | B2 | 2/2012 | Klotz et al. |
| 8,137,246 | B2 | 3/2012 | Kruijsen et al. |
| 8,353,807 | B2 | 1/2013 | Kruijsen et al. |
| 8,382,694 | B2 | 2/2013 | Wenger |
| 8,826,568 | B1 | 9/2014 | Flatley |
| 9,149,384 | B2 | 10/2015 | Wenger |
| 2002/0129821 | A1 | 9/2002 | Trieloff |
| 2003/0204157 | A1* | 10/2003 | Cropper ................ A61F 5/0111 602/27 |
| 2004/0134500 | A1 | 7/2004 | Ingimundarson et al. |
| 2005/0070833 | A1 | 3/2005 | Shields |
| 2005/0126047 | A1 | 6/2005 | Kruijsen |
| 2005/0234378 | A1 | 10/2005 | Ingimundarson et al. |
| 2006/0270958 | A1 | 11/2006 | George |
| 2007/0038169 | A1 | 2/2007 | Alon et al. |
| 2007/0191193 | A1 | 8/2007 | Backes et al. |
| 2008/0300525 | A1 | 12/2008 | Shlomovitz |
| 2009/0105624 | A1 | 4/2009 | Warner |
| 2009/0112140 | A1* | 4/2009 | Gaylord ................ A61F 5/0102 602/27 |
| 2009/0247923 | A1* | 10/2009 | Lundberg ................ A61F 5/0111 602/27 |
| 2010/0076361 | A1 | 3/2010 | Kruijsen et al. |
| 2010/0087765 | A1 | 4/2010 | Gainey |
| 2010/0132170 | A1 | 6/2010 | Armistead |
| 2011/0082404 | A1* | 4/2011 | Wenger ................ A61F 5/0111 602/28 |
| 2011/0105973 | A1* | 5/2011 | Watts ................ A61F 5/0111 602/27 |
| 2012/0029401 | A1 | 2/2012 | Caldwell et al. |
| 2013/0012855 | A1* | 1/2013 | Giza ................ A61F 5/0111 602/27 |
| 2013/0035625 | A1* | 2/2013 | Kobayashi ................ A41D 13/06 602/28 |
| 2013/0138030 | A1 | 5/2013 | Wenger |
| 2013/0232733 | A1 | 9/2013 | Jacobson et al. |
| 2014/0188026 | A1* | 7/2014 | Gaylord ................ A61F 5/0111 602/27 |
| 2014/0276318 | A1 | 9/2014 | Faux |
| 2015/0374527 | A1 | 12/2015 | Wenger |
| 2016/0095735 | A1 | 4/2016 | Wenger |

FOREIGN PATENT DOCUMENTS

| | | |
|---|---|---|
| WO | WO 92/05751 | 4/1992 |
| WO | WO 93/17641 | 9/1993 |
| WO | WO 03/092560 | 11/2003 |
| WO | WO 2004/043289 | 5/2004 |
| WO | WO 2005/030088 | 4/2005 |
| WO | WO 2005/034819 | 4/2005 |
| WO | WO 2005/097014 | 10/2005 |

OTHER PUBLICATIONS

Sassi Pacer Drop Foot Support System, www.sassipacer.com, Dec. 22, 2009, 4 pages.

Footmind Elevate Drop Foot Brace, www.Footmind.com, copyright 2013, 2 pages.

Dictus, The Dictus Band, www.dictusband.com, printed Oct. 4, 2013, 1 page.

Application and File History for U.S. Appl. No. 14/874,707, filed Oct. 5, 2015, inventor Wenger.

Application and File History for U.S. Appl. No. 12/892,664, filed Sep. 28, 2010 inventor Wenger.

Application and File History for U.S. Appl. No. 13/748,759, filed Jan. 24, 2013 inventor Wenger.

* cited by examiner

ANKLE BRACE FOR ANKLE-FOOT ORTHOTIC

RELATED APPLICATION

The present application claims the benefit of U.S. Provisional Application 62/266,887, filed Dec. 14, 2015, which is hereby incorporated herein in its entirety by reference.

TECHNICAL FIELD

The disclosure relates generally to treating steppage gait in persons suffering from a foot drop condition, and more specifically, to an apparatus and related methods for supporting the front portion of the foot to prevent foot drop and alleviate the steppage gait caused by foot drop.

BACKGROUND

Foot drop is a condition in which a person is unable to lift the front portion of one or both feet during walking or running due to a neurological or muscular condition which weakens the muscles of the foot. The condition causes the front portion of the person's foot to slap down on the floor or drag across the floor during walking or running. Persons suffering from foot drop often compensate by lifting the afflicted foot higher than normally necessary when moving to prevent the dropping foot from dragging or slapping on the floor. The irregular gait caused by the foot drop and the compensating movement by the person is known as a gait abnormality.

Foot drop is typically treated by ankle-foot orthotics that either lock the person's ankle in place or support the front portion of the person's foot. However, the currently available ankle-foot orthotics often restrict the natural flexing motion of the ankle and foot during normal movement to prevent the foot drop motion, thereby replacing the gait abnormality with a different gait abnormality. Conventional ankle locking orthotics typically comprise rigid L-shaped members fitted against the back of the ankle and the underside of the foot to prevent the entire foot from flexing downwardly at the ankle. However, because the L-shape member completely prevents downward flexing of the ankle at the foot, the foot cannot make the slight downward flexing movement that naturally occurs during walking or running.

Ankle-foot orthotics which provide support to the front portion of the foot also impede the natural flexing of the foot and ankle during a natural gait. These orthotics typically comprise straps anchored to the person's calf or ankle at one end and anchored to the person's foot or shoe at the other end to provide a tensile force preventing downward motion of the foot. However, the straps used are often static or only have a limited elasticity to ensure sufficient tensile force is applied to support the front portion of the foot. The inelasticity of the straps also inhibit the natural flexing of the foot and ankle during normal movement. The limited flexibility of presently available ankle-foot orthotics effectively replace the gait abnormality with a different gait abnormality.

In addition to being overly restrictive, currently available ankle-foot orthotics are often too bulky to fit easily into shoes. Similarly, currently available ankle-foot orthotics often require numerous straps or anchors to properly secure the orthotic to the person's ankle or foot, increasing the difficulty of putting the orthotic on or taking it off. For example, the L-shaped members of ankle locking orthotics are often large and do not easily fit into shoes without extensive modification of the shoe. In addition, the rigidness of the L-shape member prevents wearers from pointing their toes to ease putting on or taking off of the shoe. Similarly, strap orthotics often employ a plurality of straps and anchors that must be attached to the shoe or foot to properly fasten the orthotic to the person's ankle and foot. The straps and the anchors may be difficult to remove from the shoe if the person wants to remove or change shoes. The complexity and the difficulty of putting on and taking off the currently available orthotics often cause wearers to spend considerable time putting on or taking off the orthotic or forgoing the orthotic altogether. Additionally, currently available ankle-foot orthotics are typically constructed as a one-size-fits-all device that is not customizable to a user, and may cause considerable pain and/or discomfort during extended use.

Accordingly, what is needed in the industry as an improved ankle-foot orthotic that can be easily donned and doffed and is customizable for the purpose of both reducing pressure points and ensuring adequate support.

SUMMARY OF THE DISCLOSURE

Embodiments of the present disclosure meet the need of the industry for an easily donned and doffed, customizable ankle-foot orthotic configured to apply a tensile force between a wearer's ankle and shoe to counteract the effects of foot drop and prevent gait abnormalities, while enabling a wearer to adjust the fit of the orthotic for the purpose of reducing pressure points while ensuring adequate support for the ankle-foot orthotic during use.

One embodiment of the disclosure provides a customizable ankle-foot orthotic for treating foot drop that enables the wearer to adjust the fit of the ankle-foot orthotic against the wearer's ankle for the purpose of reducing pressure points while ensuring adequate support. The ankle-foot orthotic includes an ankle brace, a tensioning adjustment assembly and an elastic strap. The ankle brace is adapted for installation around a wearer's ankle. The ankle brace includes an exterior face and an interior face. The interior face is positionable against the wearer's ankle. The ankle brace further includes a first wing, a second wing opposite the first wing, and a third wing anchored to the exterior face of the ankle brace at a point between the first wing and the second wing and proximate to a rear portion of the wearer's ankle when the ankle brace is installed around the wearer's ankle. The second and third wings are independently configurable to overlap and selectively coupled to a portion of the first wing to enable the wearer to customize the fit of the interior face against the wearer's ankle.

The tension adjustment assembly is positioned on the exterior face of the ankle so as to protrude outwardly from the rear of the ankle brace when the ankle brace is wrapped around the wearer's ankle. The tension adjustment assembly can include one or more strap loops.

The elastic strap operably links the ankle brace to the wearer's shoe for applying an upward resistive force to the wearer's shoe to inhibit inadvertent downward movement of the wearer's foot. The elastic strap is threaded through one or more strap loops, such that the elastic strap wraps around the exterior face of the ankle brace and extends in a downward angle to engage the wearer's shoe.

Another embodiment of the disclosure provides a method for treating foot drop with a customizable ankle-foot orthotic in a manner that enables a wearer to adjust the fit of the ankle-foot orthotic against the wearer's ankle for the purpose of reducing pressure points as well as ensuring adequate support. In the method, the ankle brace is positioned for installation around a wearer's ankle. The ankle brace includes an exterior face and an interior face. The interior face can be positioned against the wearer's ankle. The ankle brace can include a first wing, a second wing opposite the first wing, and a third wing anchored to the exterior face of the ankle brace at a point between the first wing and the second wing and proximate to a rear portion of the wearer's ankle when the ankle brace is installed around the wearer's ankle. The second wing can be coupled to a portion of the first wing in an overlapping manner. The third wing can be coupled to a portion of the first wing in an overlapping manner. The elastic strap can be threaded through one or more strap loops of a tension adjustment assembly. The tension adjustment assembly can be positioned on the exterior face of the ankle brace, so as to protrude outwardly from the rear of the ankle brace when the ankle brace is wrapped around the wearer's ankle. The elastic strap can be coupled to the wearer's shoe, so as to wrap around the exterior face of the ankle brace and extended a downward angle to engage the wearer's shoe, thereby applying an upward resistive force to the wearer's shoe to inhibit inadvertent downward movement of the wearer's foot.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which.

Figure 1:
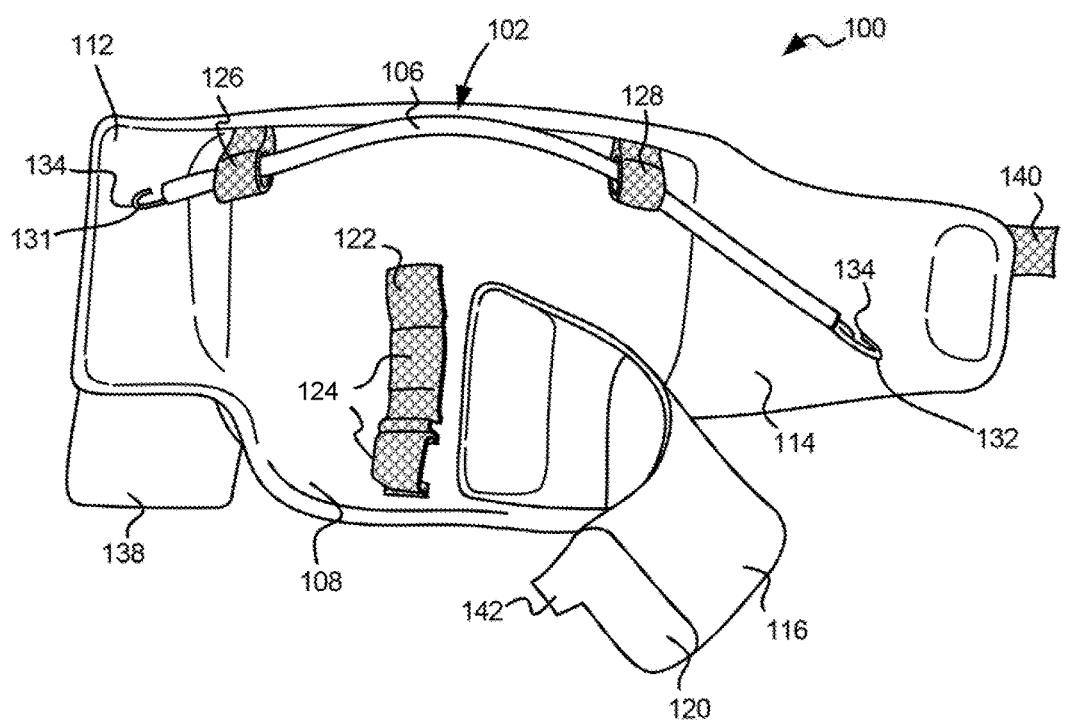
FIG. 1 depicts a perspective view of an ankle-foot orthotic in an unrolled configuration presenting the exterior face of the orthotic in accordance with an embodiment of the disclosure.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Figure 2:
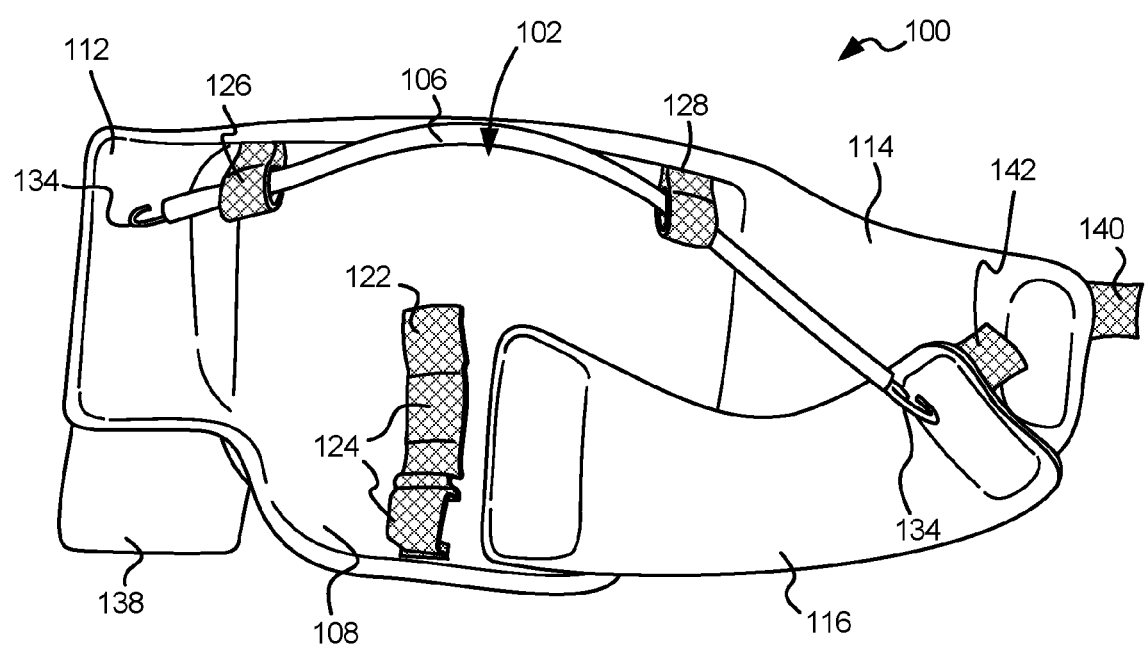
FIG. 2 depicts a perspective view of the ankle-foot orthotic of FIG. 1 in an unrolled configuration presenting the exterior face.
Figure 3:
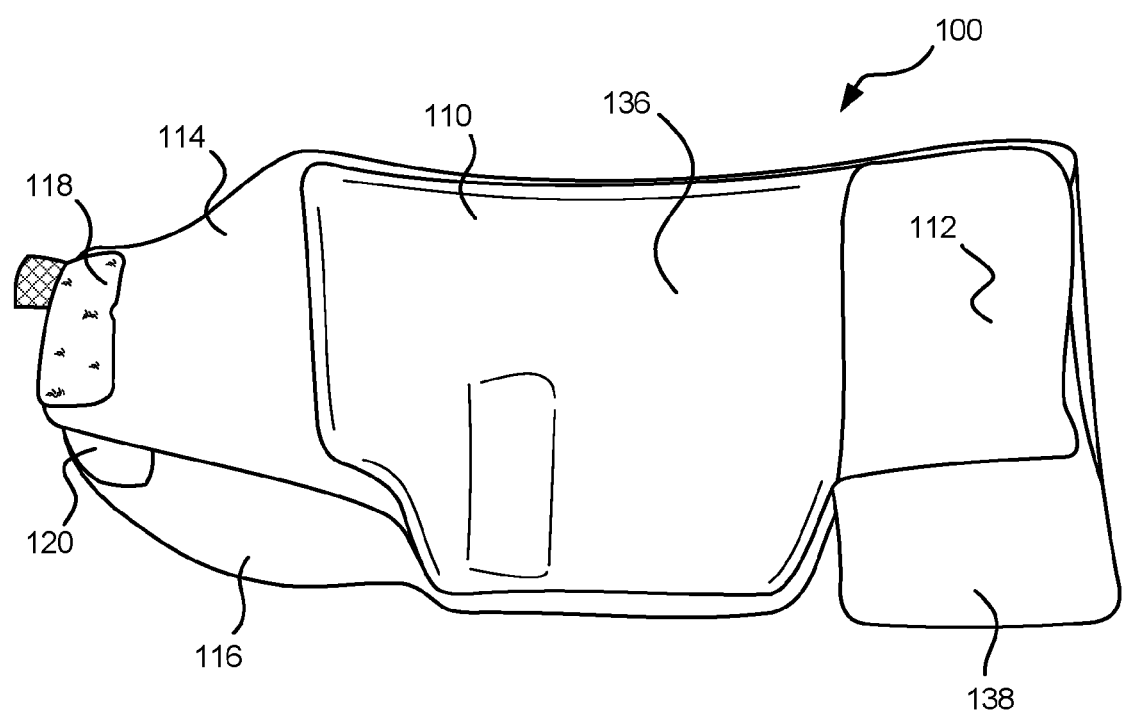
FIG. 3 depicts a perspective view of the ankle-foot orthotic of FIG. 1 in an unrolled configuration presenting the interior face.

Referring to FIGS. 1-3, an ankle-foot orthotic 100 is depicted in accordance with an embodiment of the disclosure. The ankle-foot orthotic 100 can be customizable, and can enable a wearer to adjust the fit of the ankle-foot orthotic 100 against the wearer's ankle for the purpose of reducing pressure points while ensuring adequate support in the treatment of foot drop or similar medical conditions. The ankle-foot orthotic 100 can be configured to support weakened muscles in a user's leg and foot by providing support beneath the wearer's foot or shoe, or by applying a pulling force to the top of the wearer's shoe, while at the same time enabling the wearer's foot or shoe to flex normally when walking. The pulling force is typically provided by anchoring the front or top of the wearer's foot or shoe to the wearer's ankle.

In one embodiment, the ankle-foot orthotic 100 includes an ankle brace 102, a tension adjustment assembly 104, and an elastic strap 106. Ankle brace 102 can include an exterior face 108 (as depicted in FIGS. 1-2) and an interior face 110 (as depicted in FIG. 3). In one embodiment, ankle brace 102 can include a first wing 112, a second wing 114, and a third wing 116. First wing 112 and second wing 114 can extend from opposite sides of ankle brace 102.

Third wing 116 can have a proximate end anchored to the exterior face 108 of ankle brace 102 at a point between the first wing 112 and the second wing 114 and proximate to a rear portion of the wearer's ankle when the ankle brace 102 is installed around the wearer's ankle. For example, in one embodiment, the third wing 116 can extend substantially parallel to the second wing 114. In another embodiment, the third wing 116 can be curved in shape (as depicted in FIG. 2), relative to the second wing 114, thereby imparting an upward or lifting force on the back of the wearer's ankle, when the ankle brace is installed around the wearer's ankle. Accordingly, in one embodiment, a distal end of the third wing 116 can terminate at a position proximate to the termination of second wing 114, for example below or above the second wing 114 when the ankle brace 102 is installed around the wearer's ankle.

Other ankle-foot orthotic 100 configurations are also contemplated. For example, portions of the above described ankle-foot orthotics 100 can be combined with portions of the embodiments disclosed in U.S. Pat. Nos. 8,382,694 and 9,149,384, and pending U.S. patent application Ser. Nos. 14/754,830 and 14/874,707, the contents of which are incorporated by reference herein.

In one embodiment, first wing 112 can further comprise an extension 138 configured to be positioned proximate to the top of a wearer's shoe when the ankle brace is wrapped around the wearer's ankle and can be configured reduce chafing between the wearer's shoe and the ankle brace 102. Extension 138 can similarly support the ankle brace 102 to inhibit the ankle brace 102 from sliding down the wearer's ankle during use.

In one embodiment, the second and third wings 114, 116 are independently configurable to overlap and selectively couple to a portion of the first wing 112, in order to enable the wearer to customize the fit of the interior face 110 against the wearer's ankle 202, thereby reducing pressure points while ensuring adequate support. Second wing 114 and third wing 116 can include first ankle brace fastener 118 and second ankle brace fastener 120 for releasably engaging the second wing 114 and the third wing 116 to the first wing 112 such that the ankle brace 102 forms a generally cylindrical shape around a wearer's ankle 202. Ankle brace fasteners 118 and 120 can comprise, for example, hook and loop fasteners (e.g., VELCRO), elastic fasteners, and/or button fasteners. Ankle brace 102 can be constructed of an elastic material configured to maintain tension around the wearer's ankle, thereby providing support to the wearer, while maintaining the position of the ankle brace 102 on the wearer's ankle.

In one embodiment, second wing 114 can include tab 140, and third wing 116 can include tab 142. Tabs 140 and 142 can be configured to assist the wearer in placement of second and third wing 114, 116 in the desired position for the wearer.

In one embodiment, the ankle brace 102 can further comprise an ankle pad 136 configured to provide additional support and/or alleviate discomfort. The ankle pad 136 can be constructed of foam, mesh, inflatable bladder, or other cushioning material to provide support and/or alleviate discomfort. The ankle pad 136 can be disposed on the interior face 110 of the ankle brace 102, such that the ankle pad 136 is positioned between the ankle brace 102 and the wearer's ankle, when the ankle brace is wrapped around the wearer's ankle. In this configuration, the ankle pad 136 inhibits the elastic strap 106 from chafing and/or causing other discomfort to the wearer's ankle in use.

The tension adjustment assembly 104 can be positioned on the exterior face 108 of the ankle brace 102, so as to protrude outwardly from the rear of the ankle brace 102 when ankle brace 102 is wrapped around the wearer's ankle. In one embodiment, the tension adjustment assembly 104 can include one or more strap loops 122, 124, 126, and 128.

A primary strap loop 122 can be disposed on the exterior face 108 of the ankle brace 102 between the first wing 112 and the second wing 114. The primary strap loop 122 can comprise a plurality of subloops 124, configured to enable a user to customize routing of the elastic strap 106, and thereby the tension and fit of the elastic strap 106 and ankle-foot orthotic 100. Secondary strap loops 126 and 128 can also be disposed on the exterior face 108 of the ankle brace 102, such that routing the elastic strap 106 through the primary strap loop 122 and the secondary strap loops 126 and 128 positions the elastic strap 106 in a U-shaped configuration. In other embodiments, elastic strap 106 can be routed through secondary strap loops 126 and 128 only, and not through primary strap loop 122.

Elastic strap 106 can define a first end 130 and a second end 132. In one embodiment, elastic strap 106 comprises an elastic material for applying and/or maintaining a variable tensile force between a wearer's ankle and foot. The elastic strap 106 can be sufficiently elastic to provide sufficient tensile force to inhibit the wearer's foot from inadvertently dropping due to foot drop, but has sufficient flexibility to enable the wearer to flex their foot and ankle as needed. In one embodiment, a variety of elastic straps 106 can be interchanged according to the particular tensile force required to inhibit gait abnormalities of specific wearers or provide the desired flexibility for the wearer. As such, a wearer can walk or run using the ankle-foot orthotic 100 with a more natural flexing of the foot and ankle.

In one embodiment, the elastic strap 106 can include one or more hook fasteners 134 disposed on at least one of the first and second ends 130, 132 of the elastic strap 106. Hook fasteners 104 can be adapted to engage any aperture, lobe or loop structure on the wearer's shoe, thereby operably coupling the ankle brace 102 to the wearer's shoes. In one embodiment, the hook fasteners 134 can be configured to facilitate easy attachment and removal of the hook fastener 134 from the wearer's shoe.

Figure 4A:
FIGS. 4A-F depict perspective views of the ankle-foot orthotic of FIG. 1 being attached to a user's ankle and foot.
Figure 4B:
Figure 4C:
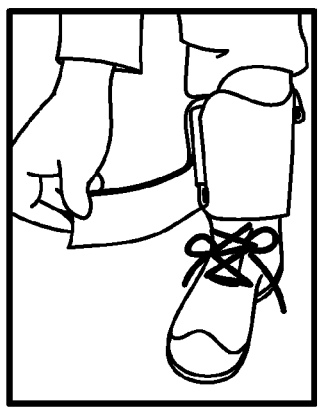
Figure 4D:
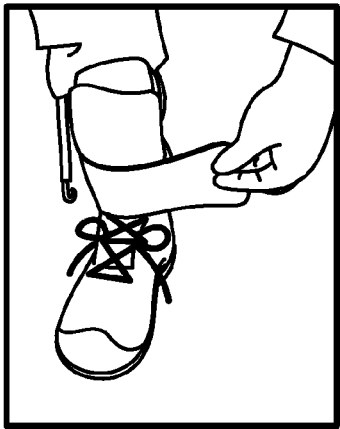
Figure 4E:
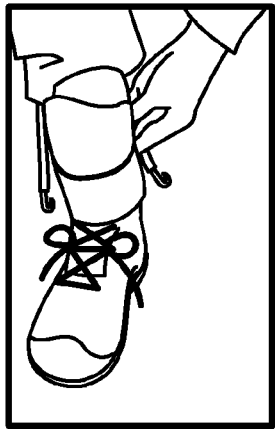
Figure 4F:
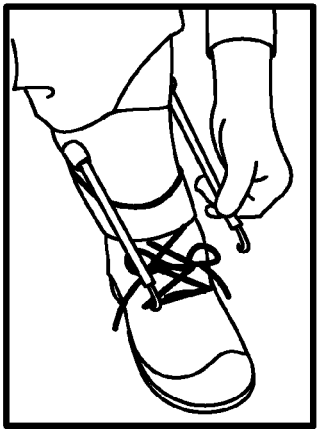
Figure 5A:
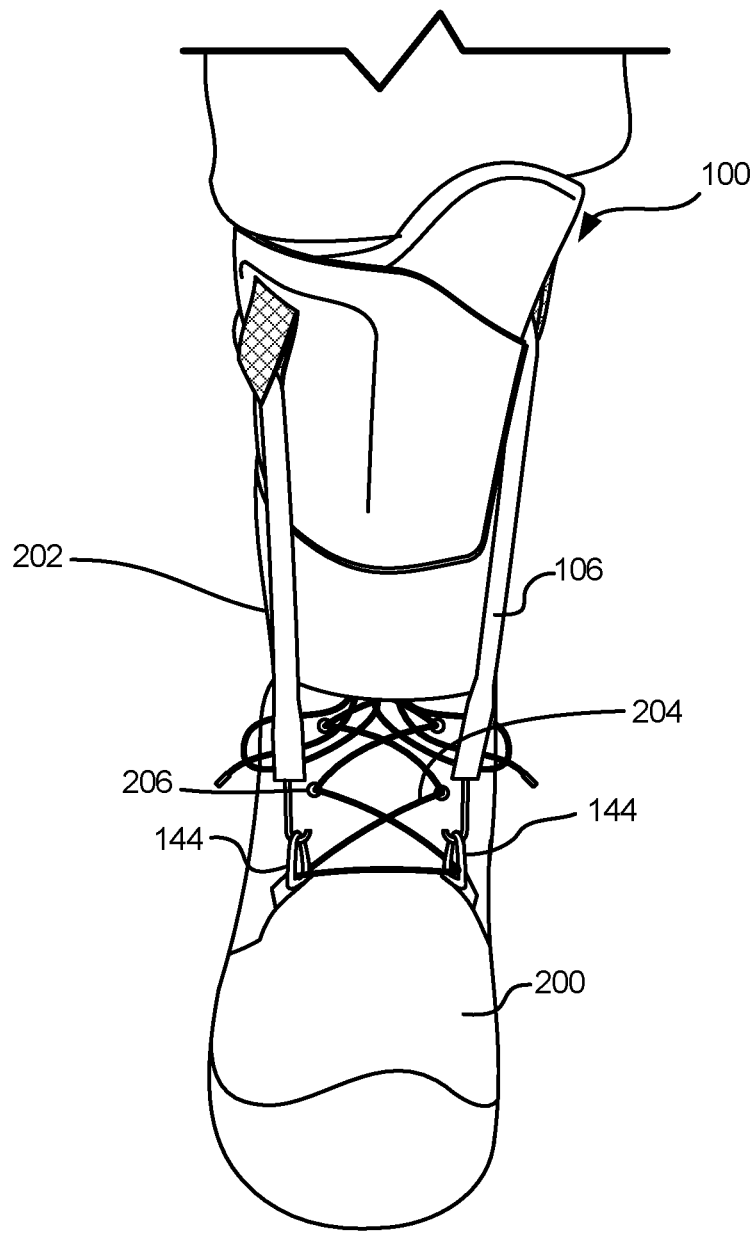
FIG. 5A depicts a front view of an ankle-foot orthotic in accordance with an embodiment of the disclosure.
Figure 5B:
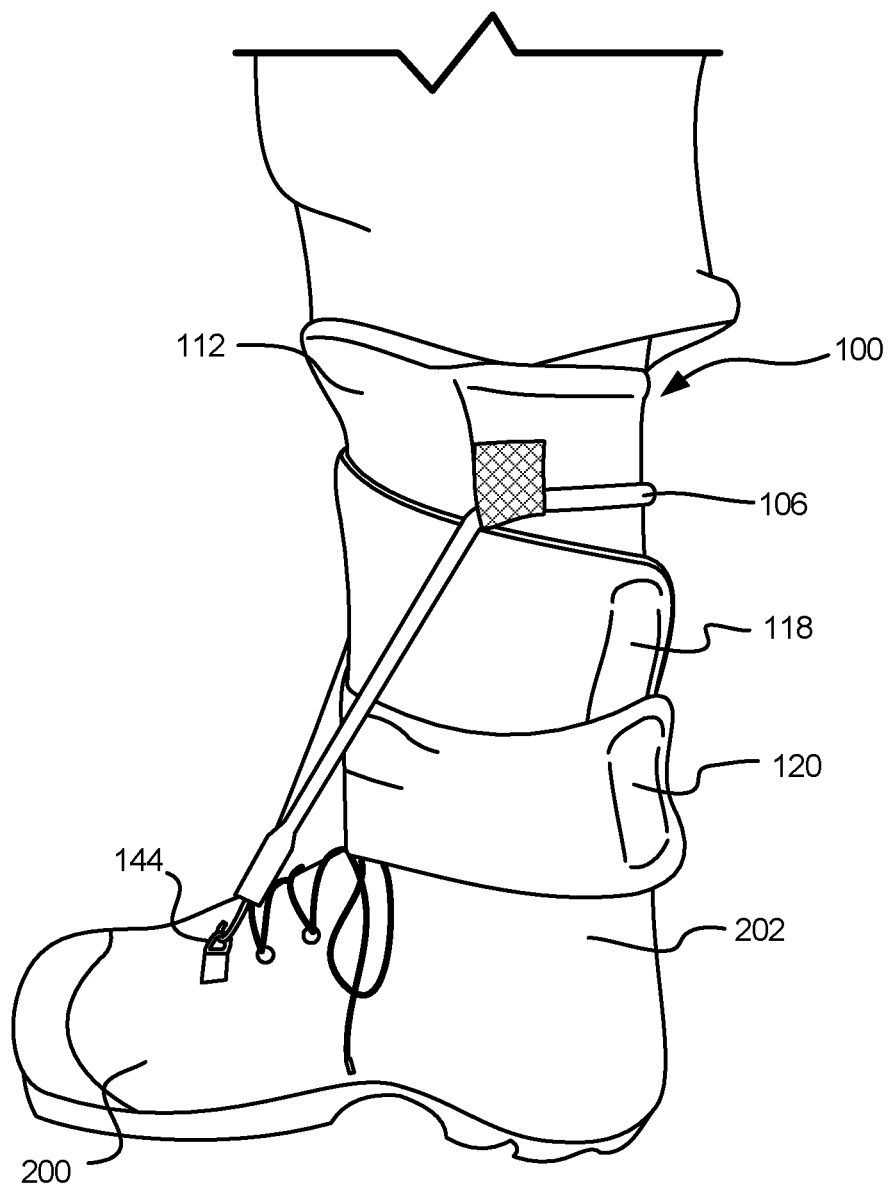
FIG. 5B depicts a left side view of the ankle-foot orthotic of FIG. 5A.
Figure 5C:
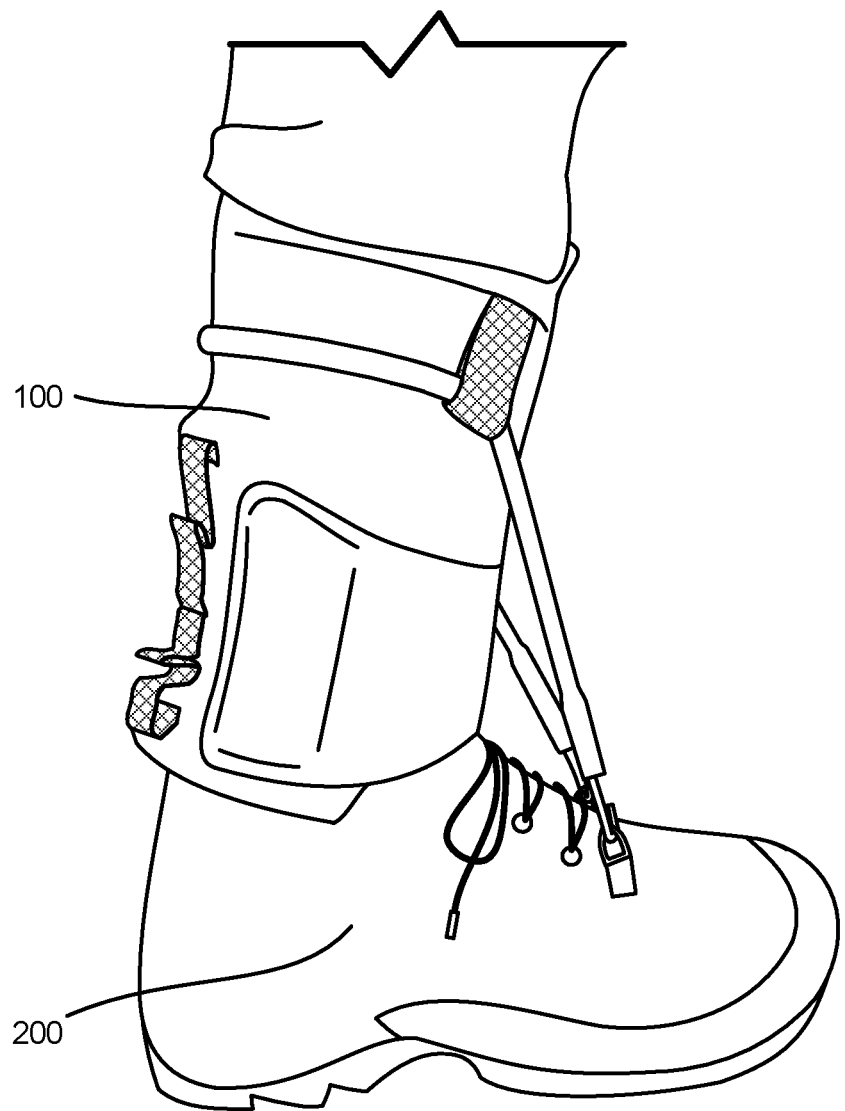
FIG. 5C depicts a right side view of the ankle-foot orthotic of FIG. 5A.
Figure 5D:
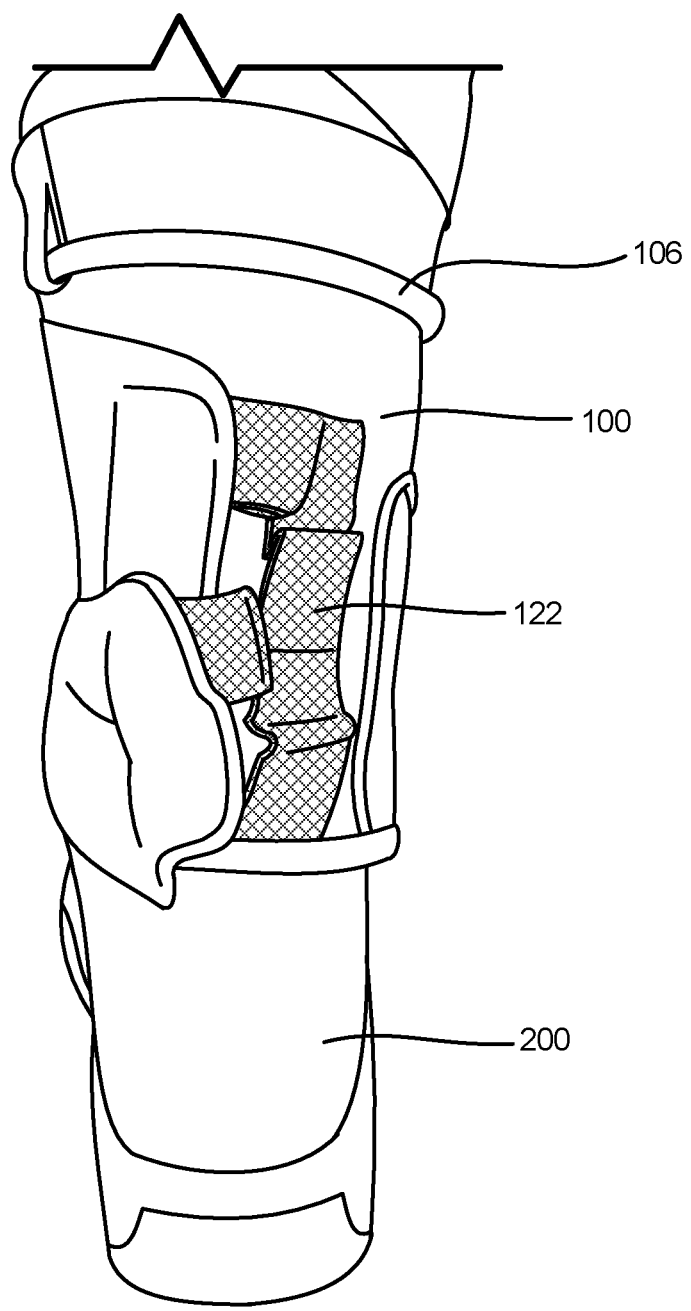
FIG. 5D depicts a rear view of the ankle-foot orthotic of FIG. 5A.

Referring to FIGS. 4A-F, in operation, the ankle brace 102 is positioned for installation around a wearer's ankle 202, such that the interior face 110 is positioned against the wearer's ankle 202. A portion of the second wing 114 is coupled to a portion of the first wing 112 in an overlapping manner (as depicted in FIGS. 4A-B). A portion of the third wing 116 is coupled to a portion of the first wing in an overlapping manner (as depicted in FIGS. 4C-D). Elastic strap 106 is threaded through one or more strap loops of the tensioning adjustment assembly 104 (as depicted in FIG. 4E). The elastic strap is coupled to the wearer's shoe 200, such that the elastic strap wraps around the exterior face 108 of the ankle brace 102 and extends in a downward ankle to engage the wearer's shoe 200, so as to apply an upward resistive force to the wearer's shoe 200 thereby inhibiting inadvertent downward movement of the wearer's foot.

In an alternative embodiment, the first, second and third wings 112, 114 and 116 can be wrapped around the wearer's ankle 202 such that the tension adjustment assembly is positioned at the front of the wearer's ankle 202.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Referring to FIGS. 5A-D, a front view, left side view, right side view, and rear view of an ankle-foot orthotic 100 positioned on a wearer is depicted in accordance with an embodiment of the disclosure. As depicted, the wearer's shoes 200 can include laces 204 and eyelets 206 for receiving shoe laces 204. Hook fasteners 134 can engage at least one of the laces 204, eyelets 206, or any other looped structure commonly found on the wearer's shoes 200. As further depicted, in one embodiment, at least one ring anchor 144 can be threaded through at least one of the eyelets 206 for coupling to the hook fasteners 134. The ring anchor 144 can be moved to whichever eyelet 206 best suits the needs of the wearer.

The magnitude of the tensile force of the elastic strap 106 can be adjusted by threading the elastic strap 106 through the various strap loops 122, 126 and 128 of the tension adjustment assembly 104. For example, in one embodiment, the primary strap loop 122 and the secondary strap loops 126 and 128 can bend the elastic strap into a U-shaped configuration, which can provide an upward or lifting force on the back of the ankle brace 102 positioned on the rear of the wearer's ankle during use. Threading the elastic strap 106 through the various combinations of strap loops 122, 126 and 128, including the various sub loops 124, can change the effective tensile force applied between the wearer's ankle 202 and the wearer's shoe 200. Optionally, as depicted, the elastic strap can be threaded through only the secondary strap loops 126 and 128, thereby bypassing primary strap loop 122.

Figure 6:
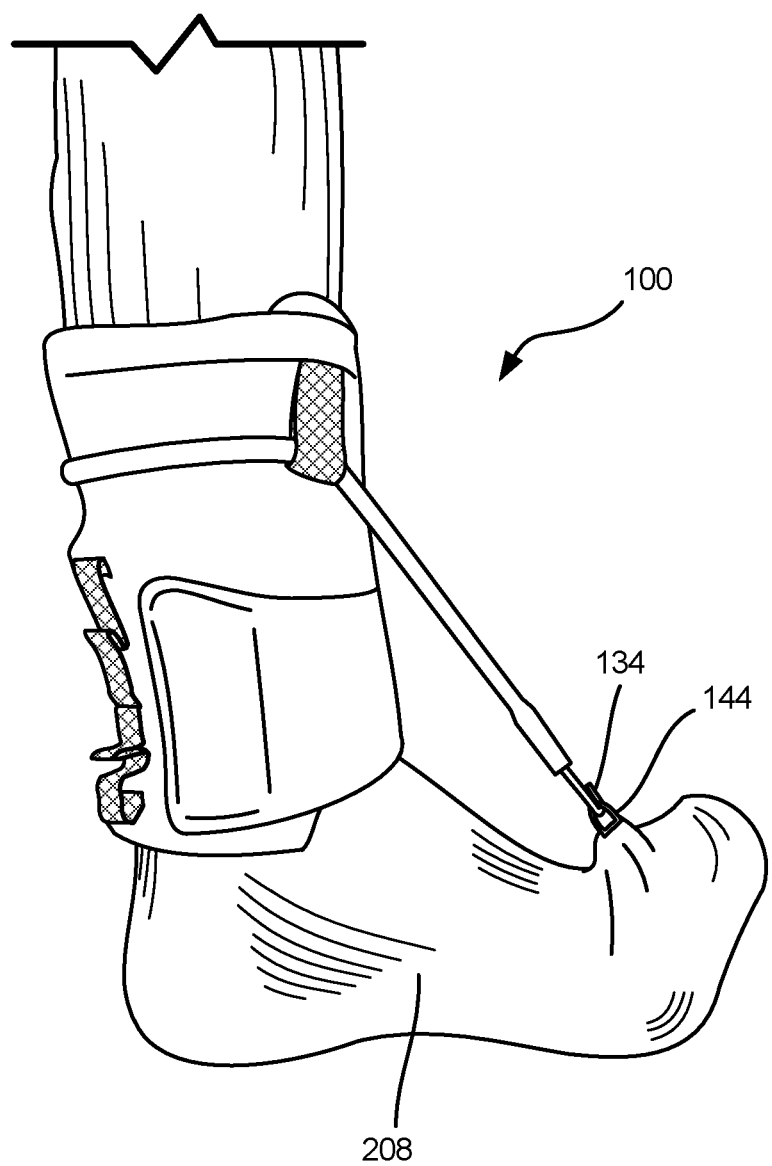
FIG. 6 depicts an ankle-foot orthotic operably coupled to a wearer's sock in accordance with an embodiment of the disclosure.

Referring to FIG. 6, an ankle-foot orthotic 100 is operably coupled to a wearer's sock 208 in accordance with an embodiment of the disclosure, thereby enabling the ankle-foot orthotic 100 to be worn without a shoe. In this embodiment, ring anchors 144 can be operably coupled to a portion of the sock 208, for example proximate to an area between the metatarsals and phalanges of the wearer's foot. The ankle-foot orthotic 100 can be operably coupled to the wearer's ankle 202 as previously described. The hook fasteners 134 can then be operably coupled to the ring anchors 144.

Figure 7:
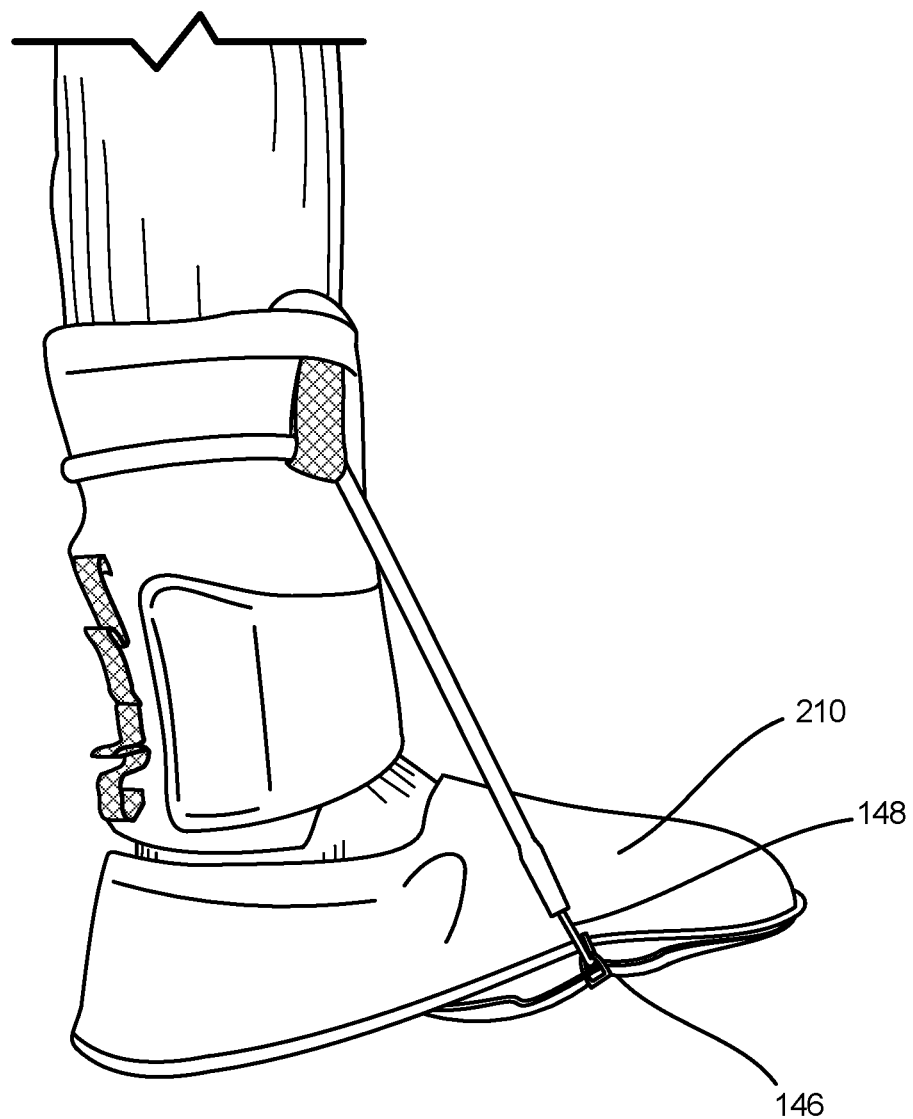
FIG. 7 depicts an ankle-foot orthotic operably coupled to a wearer's slipper in accordance with an embodiment of the disclosure.

Referring to FIG. 7, an ankle-foot orthotic 100 is operably coupled to a slipper 210 in accordance with an embodiment of the disclosure. In this embodiment, a semi-rigid pad 146 having a pair of connection loops 148 is positioned beneath a forward portion of a wearer's foot, for example proximate to an area between the metatarsals and phalanges of the wearer's foot. In some embodiments, the semi-rigid pad 146 can be operably or fixedly coupled to the slipper 210. In other embodiments, the semi-rigid pad 146 can be positioned directly beneath a wearer's foot, without the use of a slipper, so that the wearer is barefoot. In one embodiment, the semi-rigid pad 146 can have a textured or nonskid bottom surface, to provide traction with the ground during use. In one embodiment, the semi-rigid pad 146 can have a textured, nonskid, or tacky top surface to provide sufficient contact with the wearer's foot or slipper 210 in a manner that reduces the likelihood that semi-rigid pad 146 will move or shift in position during use. In this embodiment, the ankle-foot orthotic 100 can be operably coupled to the wearer's ankle 202 as previously described. The pair of hook fasteners 134 can then be operably coupled to the pair of connection loops 148.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A customizable ankle-foot orthotic for treating foot drop that that enables a wearer to adjust the fit of the ankle-foot orthotic against the wearer's ankle for the purpose of reducing pressure points while ensuring adequate support, the ankle-foot orthotic comprising:
an ankle brace adapted for installation around a wearer's ankle, the ankle brace including an exterior face and an interior face, the interior face positionable against the wearer's ankle, the ankle brace further including a first wing, a second wing opposite the first wing, and a third wing anchored to the exterior face of the ankle brace at a point between the first wing and the second wing and proximate to a rear portion of the wearer's ankle when the ankle brace is installed around the wearer's ankle, wherein the second and third wings are independently configurable to overlap and each including a distal end selectively coupleable to a portion of the first wing proximate to a rear portion of the wearer's ankle when the ankle brace is installed around the wearer's ankle such that the ankle-foot orthotic presents a generally cylindrical shape around the wearer's ankle, enabling the wearer's foot or shoe to flex normally when walking, and enabling the wearer to customize the fit of the interior face against the wearer's ankle;
a tension adjustment assembly positioned on the exterior face of the ankle brace so as to protrude outwardly from the rear of the ankle brace when the ankle brace is wrapped around the wearer's ankle, the tension adjustment assembly including one or more strap loops; and
an elastic strap operably linking the ankle brace to a wearer's shoe for applying an upward resistive force to the wearer's shoe to inhibit inadvertent downward movement of a wearer's foot, wherein the elastic strap is threadable through the one or more strap loops such that the elastic strap wraps around the exterior face of the ankle brace and extends at a downward angle to engage the wearer's shoe.

2. The ankle-foot orthotic of claim 1, wherein the first wing comprises a flap proximate a top of the wearer's foot when the ankle brace is installed around the wearer's ankle.

3. The ankle-foot orthotic of claim 1, further comprising a built-in support integrated into the ankle brace and comprising a saddle-shape for contouring to the wearer's ankle.

4. The ankle-foot orthotic of claim 1, wherein the second and third wings each comprise an adhering surface adapted to releasably adhere to the first wing.

5. The ankle-foot orthotic of claim 1, wherein the elastic strap defines a first end and a second end, each further comprising at least one hook fastener for releasably engaging any looped structures on the shoe.

6. The ankle-foot orthotic of claim 5, wherein the tension adjustment assembly further comprises:
a first secondary strap loop for receiving the elastic strap; and
a second secondary strap loop for receiving the elastic strap;
wherein a portion of the elastic strap is bendable into a u-shape by threading the elastic strap through one of the sub-loops of the primary strap loop and the secondary strap loops, wherein changing the size of the u-shaped portion changes the upward resistive applied by the elastic strap.

7. The ankle-foot orthotic of claim 1, wherein the tension adjustment assembly comprises a primary strap loop having a plurality of sub-loops.

8. The ankle-foot orthotic of claim 7, wherein threading the elastic strap through different sub-loops of the primary strap loop changes the size of the u-shaped portion of the elastic strap.

9. The ankle-foot orthotic of claim 8, further comprising one or more engagement mechanisms positionable on the wearer's shoe configured to couple with at least one of the hook fasteners.

10. The ankle-foot orthotic of claim 1, wherein the elastic strap includes a first hook fastener and a second hook fastener positioned at opposite ends of the elastic strap.

11. The ankle-foot orthotic of claim 10, wherein one of the one or more engagement mechanisms is a ring anchor.

12. A method of treating foot drop with a customizable ankle-foot orthotic, in a manner that enables a wearer to adjust the fit of the ankle-foot orthotic against the wearer's ankle for the purpose of reducing pressure points while ensuring adequate support, the method comprising:
  positioning and ankle brace for installation around a wearer's ankle, wherein the ankle brace includes an exterior face and an interior face, the interior face positioned against the wearer's ankle and including a first wing, a second wing opposite the first wing, and a third wing anchored to the exterior face of the ankle brace at a point between the first wing and the second wing and proximate to a rear portion of the wearer's ankle when the ankle brace is installed around the wearer's ankle, the second wing and the third wing each including distal ends;
  coupling the distal end of the second wing to a portion of the first wing proximate to a rear portion of the wearer's ankle in an overlapping manner;
  coupling the distal end of the third wing to a portion of the first wing proximate to a rear portion of the wearer's ankle in an overlapping manner independently of the second wing, with the ankle-foot orthotic presenting a generally cylindrical shape around the wearer's ankle and the independent configurability of the second and third wings enabling the wearer's foot or shoe to flex normally when walking, and enabling the wearer to customize the fit of the ankle-foot orthotic against the wearer's ankle;
  threading an elastic strap through one or more strap loops of a tension adjustment assembly, wherein the tension adjustment assembly is positioned on the exterior face of the ankle brace so as to protrude outwardly from the rear of the ankle brace when the ankle brace is wrapped around the wearer's ankle;
  coupling the elastic strap to the wearer's shoe, wherein the elastic strap wraps around the exterior face of the ankle brace and extends at a downward angle to engage the wearer's shoe so as to apply an upward resistive force to the wearer's shoe to inhibit inadvertent downward movement of the wearer's foot.

13. The method of claim 12, wherein the first wing comprises a flap proximate a top of the wearer's foot when the ankle brace is installed around the wearer's ankle.

14. The method of claim 12, wherein the second and third wings each comprise an adhering surface adapted to releasably adhere to the first wing.

15. The method of claim 12, wherein the elastic strap defines a first end and a second end, each further comprising at least one hook fastener for releasably engaging any looped structures on the shoe.

16. The method of claim 12, wherein the tension adjustment assembly comprises a primary strap loop having a plurality of sub-loops.

17. The method of claim 16, wherein the tension adjustment assembly further comprises:
  a first secondary strap loop for receiving the elastic strap; and
  a second secondary strap loop for receiving the elastic strap;
wherein a portion of the elastic strap is bendable into a u-shape by threading the elastic strap through one of the sub-loops of the primary strap loop and the secondary strap loops, wherein changing the size of the u-shaped portion changes the upward resistive applied by the elastic strap.

18. The method of claim 16, wherein threading the elastic strap through different sub-loops of the primary strap loop changes the size of the u-shaped portion of the elastic strap.

19. The method of claim 12, wherein the elastic strap includes a first hook fastener and a second hook fastener positioned at opposite ends of the elastic strap.

* * * * *